(12) United States Patent
Stangenes et al.

(10) Patent No.: US 8,317,810 B2
(45) Date of Patent: Nov. 27, 2012

(54) TISSUE PUNCTURE ASSEMBLIES AND METHODS FOR PUNCTURING TISSUE

(75) Inventors: Todd Raymond Stangenes, Minneapolis, MN (US); Saurav Paul, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 339 days.

(21) Appl. No.: 12/345,243

(22) Filed: Dec. 29, 2008

(65) Prior Publication Data
US 2010/0168777 A1    Jul. 1, 2010

(51) Int. Cl.
*A61B 17/34* (2006.01)
(52) U.S. Cl. ................................................ 606/167
(58) Field of Classification Search ............. 606/108, 606/170, 195, 167, 164, 113; 623/2.11
See application file for complete search history.

(56) References Cited

U.S. PATENT DOCUMENTS

| | | |
|---|---|---|
| 5,427,119 A | 6/1995 | Swartz et al. |
| 5,628,316 A | 5/1997 | Swartz et al. |
| 5,690,611 A | 11/1997 | Swartz et al. |
| 5,725,512 A | 3/1998 | Swartz et al. |
| 5,800,413 A | 9/1998 | Swartz et al. |
| 5,814,028 A | 9/1998 | Swartz et al. |
| 5,814,029 A | 9/1998 | Hassett |
| 5,833,673 A | 11/1998 | Ockuly et al. |
| 5,840,027 A | 11/1998 | Swartz et al. |
| 5,846,223 A | 12/1998 | Swartz et al. |
| 5,879,296 A | 3/1999 | Ockuly et al. |
| 6,090,084 A | 7/2000 | Hassett et al. |
| 6,156,018 A | 12/2000 | Hassett |
| 6,200,315 B1 | 3/2001 | Gaiser et al. |
| 6,203,531 B1 | 3/2001 | Ockuly et al. |
| 6,526,302 B2 | 2/2003 | Hassett |

(Continued)

FOREIGN PATENT DOCUMENTS

WO    2004026134    4/2004

OTHER PUBLICATIONS

Sosa E., et al., "Epicardial Mapping and Ablation Techniques to Control Ventricular Tachycardia, J. Cardiovasc Electrophysiol", vol. 16, pp. 449-452, Apr. 2005.

(Continued)

*Primary Examiner* — Ryan Severson
*Assistant Examiner* — Anh Dang
(74) *Attorney, Agent, or Firm* — Wiley Rein LLP

(57) ABSTRACT

A tissue puncture assembly includes an elongate tubular member having a lumen, a distal portion having a side wall, a side port opening extending through the side wall and, and a guiding surface having a distal end that extends adjacent to a distal edge of the side port opening. The tissue puncture assembly further includes a flexible puncture member insertable through the lumen of the elongate tubular member. The flexible puncture member deflects upon contacting the guiding surface to exit the elongate tubular member through the side port in a lateral direction relative to a longitudinal direction of the elongate tubular member. The tissue puncture member is capable of puncturing tissue at an oblique angle. The tissue puncture member may further adopt a pre-formed shape at its distal end to prevent inadvertent puncture of tissue and to maintain access to the puncture site. The transseptal puncture assembly may include various sensors to identify tissue structures and precisely locate the desired puncture site.

18 Claims, 6 Drawing Sheets

U.S. PATENT DOCUMENTS

| | | | |
|---|---|---|---|
| 6,554,326 B1 * | 4/2003 | Goldman | 292/144 |
| 6,752,804 B2 * | 6/2004 | Simpson et al. | 606/34 |
| 7,008,381 B2 * | 3/2006 | Janssens | 600/564 |
| 7,276,064 B2 | 10/2007 | Paul et al. | |
| 2001/0056232 A1 | 12/2001 | Lardo et al. | |
| 2002/0169377 A1 | 11/2002 | Khairkhahan et al. | |
| 2003/0144657 A1 | 7/2003 | Bowe et al. | |
| 2003/0181942 A1 | 9/2003 | Sutton et al. | |
| 2004/0059235 A1 * | 3/2004 | Saadat | 600/500 |
| 2004/0133113 A1 | 7/2004 | Krishnan | |
| 2005/0101984 A1 | 5/2005 | Chanduszko et al. | |
| 2005/0149097 A1 | 7/2005 | Regnell et al. | |
| 2005/0177182 A1 | 8/2005 | van der Burg et al. | |
| 2006/0009715 A1 | 1/2006 | Khairkhahan et al. | |
| 2006/0009737 A1 | 1/2006 | Whiting et al. | |
| 2006/0064062 A1 | 3/2006 | Gurusamy et al. | |
| 2006/0095052 A1 | 5/2006 | Chambers | |
| 2006/0276710 A1 | 12/2006 | Krishnan | |
| 2006/0276749 A1 * | 12/2006 | Selmon et al. | 604/164.01 |
| 2007/0270741 A1 | 11/2007 | Hassett et al. | |
| 2007/0270751 A1 | 11/2007 | Stangenes et al. | |
| 2008/0103400 A1 | 5/2008 | Krishnan | |

OTHER PUBLICATIONS

Hanaoka T., et al., "Shifting of Puncture Site in the Fossa Ovalis During Radiofrequency Catheter Ablation", Jpn Heart J., 44 (5): 673-680, 2003.

Burnett J., et al,, "Intracardiac Echocardiography 101: The Beginner's Guide to ICE Imaging and Cardiac Structure Recognition", EP Lab Digest, vol. 5, May 2005, available at http://www.eplabdigest.com/article/4148.

Szili-Torok, T., et al., "Transseptal Left Heart Catheterisation Guided by Intracardiac Echocardiography", Heart, 86(5): e11 (2001) (abstract).

Liang, K., et al., "Intra-Cardiac Echocardiography Guided Transseptal Puncture in Patients with Dilated Left Atrium Undergoing Percutaneous Transvenous Mitral Commissurotomy", Int'l. J. Cardiology, 117(3): 418-421 (2003) (abstract).

Daoud, Emile., et al., "Intracardiac Echocardiography to Guide Transseptal Left Heart Catheterization for Radiofrequency Catheter Ablation", J. Cardio. Electrophysiology, 10 (3): 358-363, Apr. 2007 (abstract).

* cited by examiner

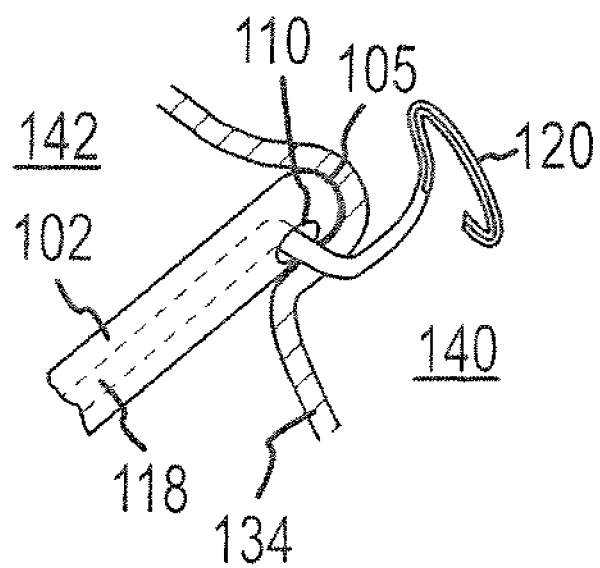

TISSUE PUNCTURE ASSEMBLIES AND METHODS FOR PUNCTURING TISSUE

BACKGROUND OF THE INVENTION a. Field of the Invention

The present invention pertains generally to devices and methods for puncturing tissue within the body. More particularly, the invention is directed to devices and methods for puncturing the interatrial septum and/or pericardial sac to facilitate atrial and/or epicardial ablation.

b. Background Art

The traditional method for gaining access to the left atrium is to puncture the interatrial septum at the location of the fossa ovalis. Access to the left atrium is needed for a variety of therapeutic medical procedures, for example left atrial radiofrequency catheter ablation. Nevertheless, transseptal puncture has numerous potential complications. For instance, advancing the needle beyond the interatrial septum may result in inadvertent puncture of heart structures such as the left atrial free wall. Moreover, improperly puncturing a site other than the fossa ovalis—a structure notoriously difficult to locate—may lead to certain surgical complications. Additionally, reliably verifying that puncture was successful may be complicated by a lack of left atrial access post-puncture.

Many current transseptal needle devices and assemblies do not address these concerns. For instance, some transseptal needle devices feature a needle which punctures tissue in a substantially straight orientation and cannot be manipulated to puncture tissue at an angle. In essence, a physician using such a device is puncturing the interatrial septum with little to no information regarding the precise location of heart structures beyond the interatrial septum. Moreover, the physician is uniformly using the same puncturing angle from procedure to procedure regardless of the positioning of the transseptal needle device relative to the interatrial septum.

Accordingly, there is a growing need for tissue puncture assemblies that are capable of puncturing a tissue at an oblique angle. Moreover, there is a growing need for tissue puncture assemblies that may provide more precise information regarding the location of key structures such as the left atrial free wall and the fossa ovalis. Furthermore, there is a growing need for transseptal needle devices capable of maintaining access to the left atrium post-puncture.

BRIEF SUMMARY OF THE INVENTION

The present invention provides assemblies and methods for puncturing, or piercing, tissue within the body, including transseptal needles and transseptal needle assemblies.

It is an object of the present invention to provide a tissue puncture assembly capable of puncturing a tissue at an oblique angle.

Another object of the present invention is to provide a tissue puncture assembly having an anchor for maintaining access to the puncture site.

A further object of the present invention is to provide a tissue puncture assembly capable of automatically adopting an atraumatic shape after puncturing a tissue to prevent inadvertent puncture of other tissues or structures.

Still another object of the present invention is to provide a tissue puncture assembly capable of identifying tissue structures to more precisely locate the desired puncture site.

Yet another object of the present invention is to provide a method for puncturing the interatrial septum.

A further object of the present invention is to provide a method for puncturing the pericardial sac.

A medical device includes an elongate tubular member having a lumen extending therethrough in a longitudinal direction and a flexible puncture member insertable through the lumen of the elongate tubular member. The elongate tubular member includes a distal portion having a side wall, a side port opening extending through the side wall, and a guiding surface within the lumen of the elongate tubular member. The guiding surface includes a distal end which extends adjacent to the distal edge of the side port opening.

The flexible puncture member includes a distal end, and deflects upon contacting the guiding surface to exit the elongate tubular member through the side port in a lateral direction relative to the longitudinal direction of the elongate tubular member. The flexible puncture member may be made of a shape-memory alloy such as Nitinol, and may include a lumen extending therethrough. A guidewire may be inserted through the lumen.

In one aspect, the distal end of the flexible puncture member may adopt a pre-formed shape such as a helix, flower shape, or basket shape. The distal end of the flexible puncture member may be straightenable for insertion within the elongate tubular member, but automatically adopts the pre-formed shape upon exiting the elongate tubular member. In another aspect, the distal tip of the flexible puncture member may be beveled.

In yet another aspect of the present invention, the distal portion of the elongate tubular member may include at least one electrode coupled to an impedance-measuring circuit. In another aspect, the distal portion of the elongate tubular member may include at least one pair of electrodes coupled to an impedance-measuring circuit. In still another aspect of the present invention, the distal portion of the elongate tubular member may include at least one thermal sensor coupled to a temperature-measuring circuit.

In a further aspect of the present invention, the side port opening may define an outer perimeter, which may include at least one of an electrode and a thermal sensor. In another aspect, the distal portion of the elongate tubular member includes at least one intravascular ultrasound sensor coupled to an image processor. In yet another aspect of the present invention, the distal portion of the elongate tubular member includes a plurality of ultrasound transducers in a phased array. In one aspect, the plurality of ultrasound transducers may be arranged in a linear phased array parallel to the longitudinal direction of the elongate tubular member. In another aspect, the plurality of ultrasound transducers may be arranged radially about the distal portion of the elongate tubular member in a circular phased array. In a further aspect, the distal portion of the elongate tubular member includes at least one ultrasound transducer. The ultrasound transducer or a reflective surface which deflects the signal from the ultrasound transducers may be rotatable relative to an axis of the elongate tubular member.

In another embodiment of the present invention, a method for accessing a left-side cardiac chamber from a right-side cardiac chamber includes the steps of providing a flexible puncture member contained within a lumen of an elongate tubular member, the elongate tubular member including a guiding surface within the lumen and a distal portion having a distal tip and a side port opening, inserting the elongate tubular member containing the flexible puncture member into the right-side cardiac chamber, and urging the distal tip of the elongate tubular member against the septum within the right-side chamber so that at least a portion of the septum is adjacent the side port opening.

The method may further include the step of advancing the flexible puncture member through the elongate tubular member. During this step, the flexible puncture member deflects upon contacting the guiding surface to exit the side port in a lateral direction relative to a longitudinal direction of the elongate tubular member. The method may further include the step of puncturing the portion of the septum adjacent the side port opening with the flexible puncture member. In one aspect, the flexible puncture member may puncture the septum at an oblique angle. In another aspect, the right-side cardiac chamber may be the right atrium and the septum may be the interatrial septum. In this aspect, the method includes puncturing the interatrial septum.

In a further aspect, the urging step includes urging the distal tip of the elongate tubular member against the fossa ovalis so that at least a portion of the fossa ovalis is adjacent the side port opening, and the puncturing step includes puncturing the portion of the fossa ovalis adjacent the side port opening.

In yet another aspect, the method may include using one or more sensors located on the distal portion of the elongate tubular member to detect a location of the fossa ovalis.

In another aspect of the present invention, the method further comprises the step of advancing the flexible puncture member through the interatrial septum and into the left atrium. In a further aspect, during the advancing step, the distal end of the flexible puncture member may adopt a pre-formed shape, such as a helix, a flower shape, or a basket shape, and may become anchored within the left atrium. In yet another aspect, the elongate tubular member may be advanced over the flexible puncture member such that the distal end of the flexible puncture member adopts a generally straightened state when it is contained within the elongate tubular member.

The method may further comprise the steps of inserting a guidewire through a lumen of the flexible puncture member and into the left atrium, withdrawing the elongate tubular member and flexible puncture member, providing an electrophysiology catheter such as an ablation catheter, a diagnostic catheter, or a combination ablation and diagnostic catheter, and advancing the electrophysiology catheter over the guidewire and into the left atrium.

In another aspect, the method may include the step of advancing a dilator contained within a sheath over the guidewire and into the left atrium. In this aspect, the method further includes the steps of withdrawing the guidewire and dilator, providing an electrophysiology catheter such as an ablation catheter, a diagnostic catheter, or a combination ablation and diagnostic catheter, and advancing the electrophysiology catheter through the sheath and into the left atrium.

In a further embodiment of the present invention, a method for puncturing the pericardial sac includes the steps of steps of providing a flexible puncture member contained within a lumen of an elongate tubular member, the elongate tubular member including a guiding surface within the lumen and a distal portion having a distal tip and a side port opening, inserting the elongate tubular member containing the flexible puncture member into a patient via a subxiphoid percutaneous approach, and urging the distal tip of the elongate tubular member against the pericardial sac so that at least a portion of the interatrial septum is adjacent the side port opening.

The method further includes the step of advancing the flexible puncture member through the elongate tubular member. During this step, the flexible puncture member deflects upon contacting the guiding surface to exit the side port in a lateral direction relative to a longitudinal direction of the elongate tubular member. The method further includes the step of puncturing the portion of the pericardial sac adjacent the side port opening with the flexible puncture member. In one aspect, the flexible puncture member may puncture the pericardial sac at an oblique angle. In yet another aspect, the method may include using one or more sensors located on the distal portion of the elongate tubular member to detect a location of the pericardial sac.

In another aspect of the present invention, the method further comprises the step of advancing the flexible puncture member through the pericardial sac and into the pericardial space. In a further aspect, during the advancing step, the distal end of the flexible puncture member may adopt a pre-formed shape, such as a helix, a flower shape, or a basket shape, and may become anchored within the pericardial space. In yet another aspect, the elongate tubular member may be advanced over the flexible puncture member such that the distal end of the flexible puncture member adopts a generally straightened state when it is contained within the elongate tubular member.

The method may further include the steps of inserting a guidewire through a lumen of the flexible puncture member and into the pericardial space, withdrawing the elongate tubular member and flexible puncture member, advancing a dilator contained with a sheath over the guidewire and into the pericardial space, withdrawing the guidewire and dilator, providing an electrophysiology catheter such as an ablation catheter, a diagnostic catheter, or a combination ablation and diagnostic catheter, and advancing the electrophysiology catheter through the sheath and into the pericardial space.

An advantage of the present invention is that it provides a tissue puncture assembly capable of puncturing a tissue at an oblique angle.

Another advantage of the present invention is that it provides a tissue puncture assembly having an anchor for maintaining access to the puncture site.

Still another advantage of the present invention is that it provides a tissue puncture assembly capable of automatically adopting an atraumatic shape after puncturing a tissue to prevent inadvertent puncture of other tissues or structures.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 9A-E schematically illustrates a method of puncturing tissue according to an embodiment of the present invention.

DETAILED DESCRIPTION OF THE INVENTION

Disclosed herein is a tissue puncture assembly capable of puncturing a tissue at an oblique angle. The invention will be described in connection with puncturing the interatrial septum and the pericardial sac. It is contemplated, however, that the described device and methods may be utilized to puncture any number of tissues within the body, as would be appreciated by one of ordinary skill in the art.

Figure 1:
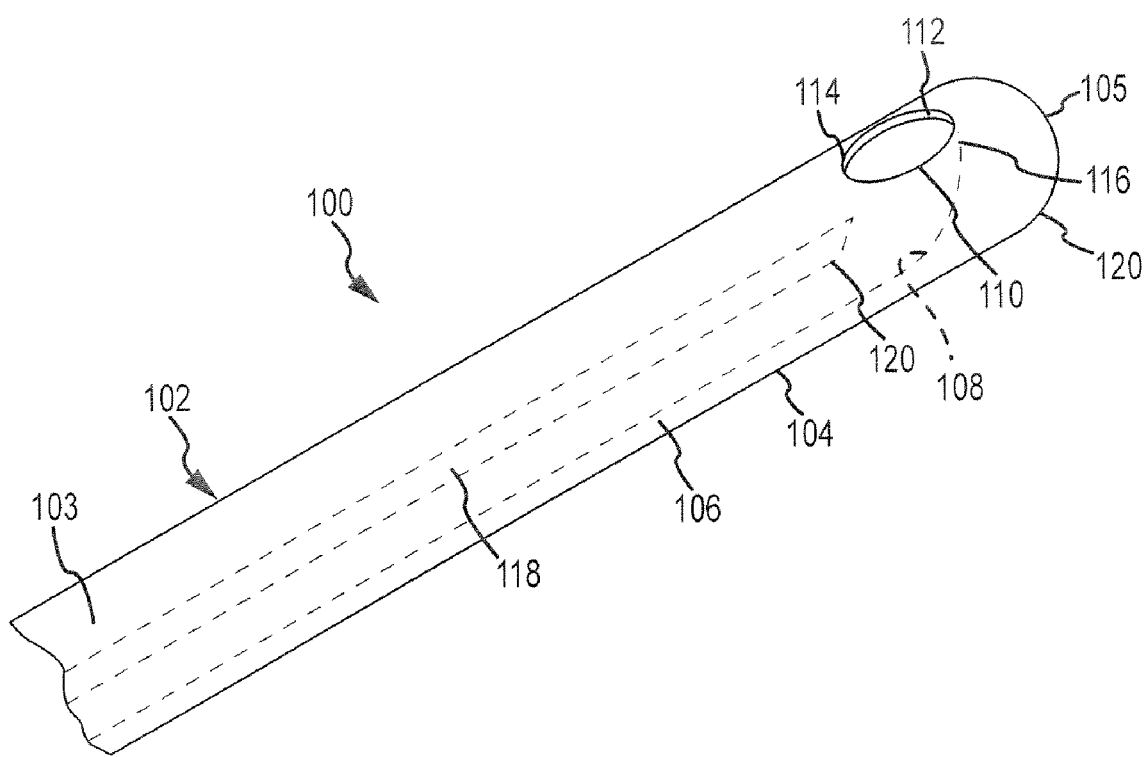
FIG. 1 is a fragmentary, isometric view of a tissue puncture assembly according to an embodiment of the present invention.
Figure 2:
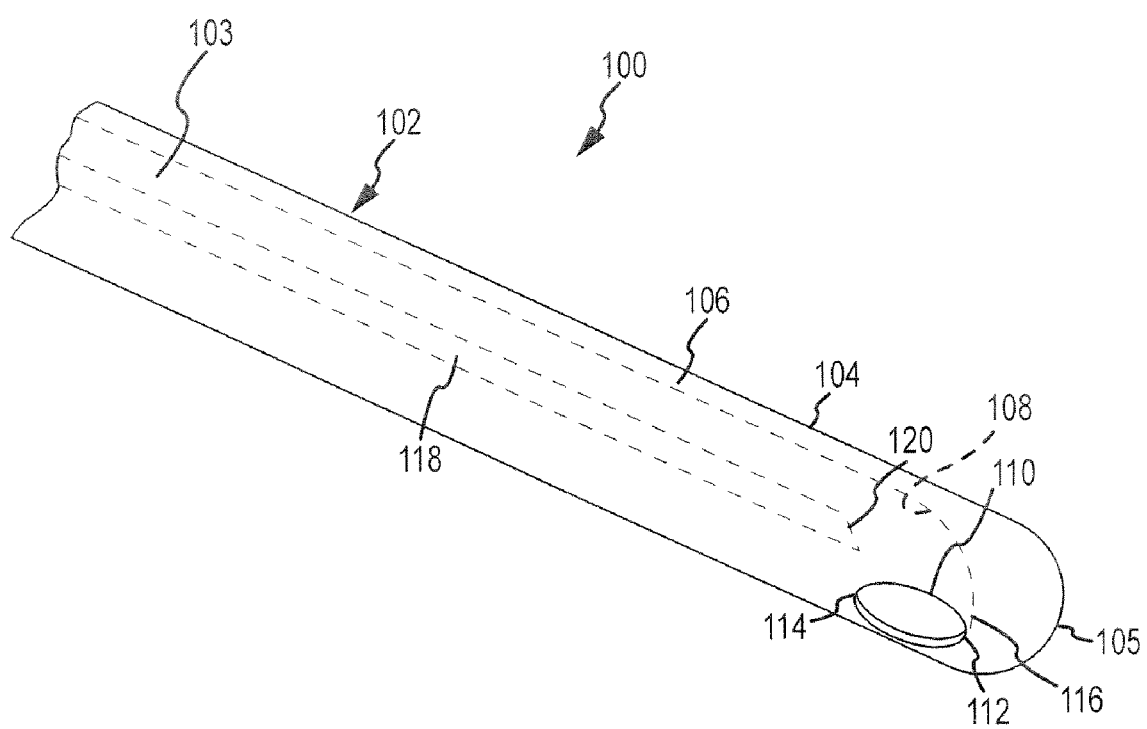
FIG. 2 is a fragmentary, isometric view of the tissue puncture assembly depicted in FIG. 1, with the side port opening shown in phantom.

Referring now to FIGS. 1-2, a tissue puncture assembly 100 includes an elongate tubular member 102 having a lumen 103 (shown in phantom) extending therethrough and a distal portion 104. The distal portion 104 includes a side wall 106, and a side port opening 110 extends through the side wall 106. The side port opening 110 has a distal edge 112 and a proximal edge 114. A guiding surface 108 is disposed within the lumen 103 of the elongate tubular member 102. The guiding surface 108 has a distal end 116 which extends adjacent to the distal edge 112 of the side port opening 110.

The tissue puncture assembly 100 also includes a flexible puncture member 118 disposed within the lumen 103 of the elongate tubular member 102. The flexible puncture member 118 has a distal tip 120 that is adapted to puncture a tissue. In one aspect, the distal tip 120 of the flexible puncture member 118 is beveled. The distal tip 120 may also be blunt. Example of a distal tip structure that are suitable for use with the present invention are described in U.S. application Ser. No. 12/117,675, filed May 8, 2008, which is incorporated herein by reference in its entirety. In another aspect, the flexible puncture member 118 includes a lumen 144 (FIGS. 3A-C) extending therethrough to permit the passage of a guidewire, or like device. The flexible puncture member 118 is slidable within the lumen 103 of the elongate tubular member 102.

Figure 4:
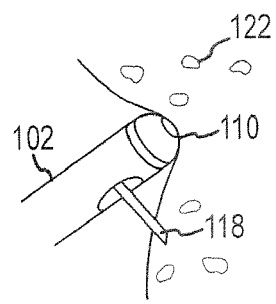
FIG. 4 illustrates a tissue puncture assembly according to an embodiment of the invention pressed against a tissue.

In one aspect, the guiding surface 108 may be wedge-shaped, curvilinear, or ramp-like. The guiding surface 108 provides a path for directing the flexible puncture member 118 through the side port opening 110, or a means for deflecting the distal tip 120 of the flexible puncture member through the side port opening 110. The guiding surface 108 may be integrally formed within the lumen 103 of the elongate tubular member 102, or may be a separate component fixed within the lumen 103 of the elongate tubular member 102 according to known methods. As illustrated in FIG. 4, in one aspect the flexible puncture member 118 may deflect upon contacting the guiding surface 108 to exit the side port opening 110 in a lateral direction relative to a longitudinal direction of the elongate tubular member 102. In another aspect, the flexible puncture member 118 may glide along the guiding surface 108 in a substantially smooth motion as the guiding surface 108 directs the flexible puncture member 118 through the side port opening 110.

The side port opening 110 facilitates placement of the flexible puncture member 118 adjacent to or in contact with a tissue to be punctured. The side port opening 110 is shaped to permit the flexible puncture member 118 to pass through to contact a tissue. Thus, the side port opening 110 may be circular, oval, or any other suitable shape. In one aspect, an inner dimension of the side port opening 110, for example, an inner diameter if the side port opening is circular, is at least about three times as large as the outer diameter of the flexible puncture member 118. In other aspects, an inner dimension of the side port opening 110 is as small as about two times the outer diameter of the flexible puncture member 118 or as large as about eight times the outer diameter of the flexible puncture member 118. The side port opening 110 should be sufficiently large to easily permit passage of the flexible puncture member 118, but not so large that it compromises the integrity of the elongate tubular member 102.

Figure 5A:
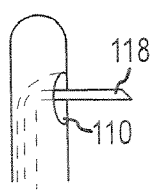
FIG. 5A depicts the distal portion of a tissue puncture assembly according to an embodiment of the present invention.
Figure 5B:
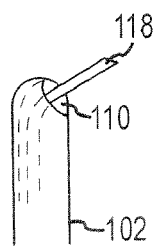
FIG. 5B illustrates the distal portion of a tissue puncture assembly according to another embodiment of the present invention.

The location of the side port opening 110 along the distal portion 104 of the elongate tubular member 102 may be varied to modify the angle at which the flexible puncture member 118 exits the side port opening 110. For example, in one aspect, the side port opening 110 extends entirely through the side wall 106 of the elongate tubular member 102, as shown in FIG. 5A. In another aspect, the side port opening 110 may extend through a portion of the distal tip 105 of the elongate tubular member 102, as shown in FIG. 5B.

Figure 6A:
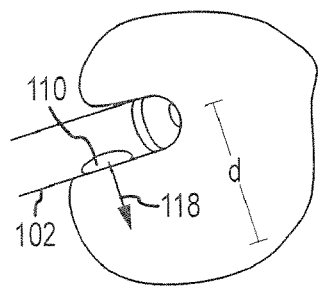
FIGS. 6A-B illustrate a tissue puncture assembly puncturing the interatrial septum from two different locations.
Figure 6B:
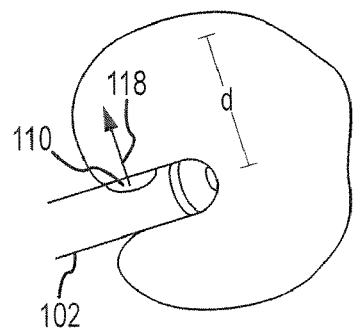

The orientation of the side port opening 110 (as depicted in FIGS. 6A-B) relative to the tissue can be varied to achieve an optimal puncture angle. For instance, the side port opening 110 can be oriented to achieve an oblique puncture angle. Puncturing a tissue at an oblique angle is advantageous in several respects. For example, the puncture angle can be tailored to the specific procedure being performed, as opposed to uniformly using the same puncture angle regardless of the type of tissue being punctured or the surrounding structures.

The distal end 120 of the flexible puncture member 118 may be designed to automatically adopt an atraumatic, pre-formed shape when it is unconstrained by the elongate tubular member 102. For example, the distal end 120 of the flexible puncture member 118 may be configured to automatically adopt a pre-formed shape after exiting the elongate tubular member 102 via the side port opening 110 and puncturing a tissue. Conversely, the distal end 120 of the flexible puncture member 118 adopts a generally straightened state when it is contained within the elongate tubular member 102. In one aspect of the present invention, the flexible puncture member 118 is made of a shape-memory alloy, for example Nitinol. One of ordinary skill in the art will appreciate, however, that any suitable shape-memory material may be used to form the flexible puncture member 118 without departing from the scope and spirit of the present invention.

Adoption of a pre-formed shape by distal end 120 is advantageous in several respects. For example, the atraumatic, pre-formed shape helps prevent inadvertent puncture of internal structures, for example the left atrial free wall during transseptal procedures. In this example, even if the flexible puncture member 118 is advanced too far beyond the fossa ovalis, the atraumatic, pre-formed shape will prevent inadvertent puncture of the left atrial free wall. Further, the pre-formed shape may also serve as a temporary anchor to maintain access to the puncture site. For example, during transseptal access procedures, the distal end 120 of the flexible puncture member 118 may adopt the pre-formed shape, thus preventing the flexible puncture member 118 from sliding back through the interatrial septum and further maintaining access to the left atrium. In the typical transseptal puncture procedure, the physician pauses after the initial puncturing step to either verify successful puncture (with pressure monitoring or contrast injection) or to advance a guidewire into the left atrium. With the distal tip 120 of the flexible puncture member 118 adopting an anchor shape, these steps may be completed more reliably.

Figure 3A:
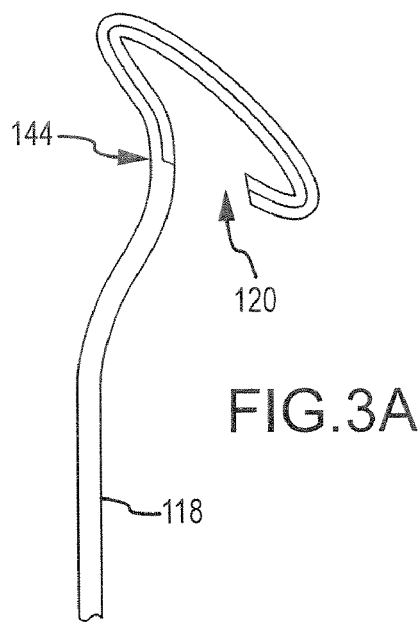
FIG. 3A illustrates a helical-shaped anchor member.
Figure 3B:
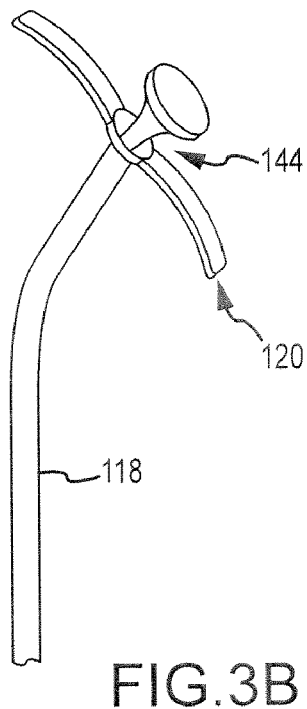
FIG. 3B depicts a flower-shaped anchor member.
Figure 3C:
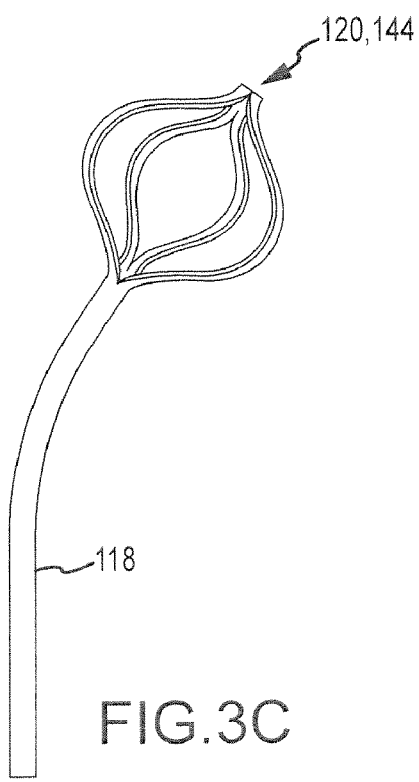
FIG. 3C illustrates a basket-shaped anchor member.

FIGS. 3A-C illustrate various pre-formed shapes that the distal end 120 of the flexible puncture member 118 may adopt according to several aspects of the present invention. In one embodiment, distal end 120 may adopt a helical shape (see FIG. 3*a*). In another embodiment, distal end 120 may adopt a flower shape (see FIG. 3*b*). In yet another embodiment, distal end 120 may adopt a basket shape (see FIG. 3*c*). A person of skill in the art will understand that the distal end 120 of the flexible puncture member can be configured to adopt various pre-formed, atraumatic shapes to achieve the objectives described herein.

Figure 7:
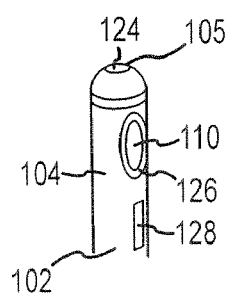
FIG. 7 is a close-up view of the distal portion of a tissue puncture assembly including sensors and/or transducers.

The tissue puncture assembly 100 of the present invention may further include various types of sensors to facilitate proper placement of the device and more precise puncturing. FIG. 7 is a close-up view of a tissue puncture assembly including sensors and/or transducers. In one embodiment, the distal portion 104 of the elongate tubular member 102 includes at least one electrode 124 coupled to an impedance-measuring circuit (not pictured). In another embodiment, the distal portion 104 of the elongate tubular member 102 includes a pair of electrodes coupled to an impedance-measuring circuit. A person of skill in the art will appreciate, however, that the distal portion 104 of the elongate tubular member may include any number of electrodes for impedance-measuring. The electrodes may be located at the distal tip 105 or proximally of the distal tip. In another aspect, an electrode 126 surrounds the perimeter of the side port opening 110. The location of the fossa ovalis may be determined by taking impedance measurements at a variety of interatrial septal locations. Because the fossa ovalis is thinner than other portions of the interatrial septum, it is characterized by a low impedance value compared to the surrounding interatrial septal tissue.

In another embodiment, the distal portion 104 of the elongate tubular member 102 includes laterally-disposed intracardiac echocardiographic (ICE) sensors. ICE sensors can visualize the characteristic fossa ovalis tenting shape. Thus, incorporating an ICE sensor array onto the distal portion 104 of the elongate tubular member 102 enables a physician to more precisely locate the fossa ovalis and/or more precisely orient the distal portion 103 of the elongate tubular member 102 for deployment of the flexible puncture member 118. In one aspect, the ICE sensor may include an array of ultrasound transducers. Specifically, the ultrasound transducer array may be arranged radially about the distal portion 104 of the elongate tubular member 102 in a circular phased array. Alternately, the ultrasound transducer array may be arranged in a linear phased array 128 parallel to the longitudinal direction of the elongate tubular member 102.

In yet a further embodiment, ICE imaging may be achieved using a single ultrasound transducer in lieu of a phased array. In particular, the distal portion 104 of the elongate tubular member 102 may include at least one ultrasound transducer which is rotatable relative to an axis of the elongate tubular member 102. Alternately, a reflective surface which deflects the signal from the ultrasound transducer may be rotatable relative to an axis of the elongate tubular member 102.

In yet another embodiment, the distal portion 104 of the elongate tubular member 102 may include at least one intravascular ultrasound (IVUS) sensor 124 coupled to an image processor (not pictured). IVUS sensors utilize ultrasound technology to visualize a variety of structures. Incorporating an IVUS sensor 124 onto the distal portion 104 of the elongate tubular member 102 enables a physician to more precisely locate the fossa ovalis and/or more precisely orient the distal portion 104 of the elongate tubular member 102 for deployment of flexible puncture member 118.

Figure 8A:
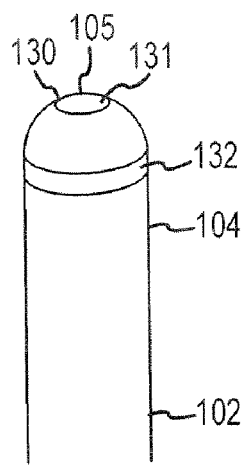
FIG. 8A depicts the distal portion of a tissue puncture assembly having a thermal sensing mechanism at the distal tip.

FIG. 8A depicts yet another embodiment of a tissue puncture assembly having a thermal sensing mechanism for locating the fossa ovalis. In this embodiment, the elongate tubular member 102 includes a first electrode 130 and a second electrode 132. The first electrode 130 is located at the distal tip 105 of the elongate tubular member 102, and the second electrode 132 is located along the distal portion 104 of the elongate tubular member 102 proximally of the first electrode 130. The first electrode 130 may be a button electrode and the second electrode 132 may be a ring electrode. The first electrode may further includes a thermal sensor 131, which may be a thermocouple, thermistor, or any other type of temperature-monitoring sensor known in the art. Alternatively, the thermal sensor 131 may be located adjacent to the first electrode 130. The first electrode 130 and the second electrode 132 create a bi-pole along the distal portion 104 of the elongate tubular member 102. When RF energy is delivered between these two poles, the adjacent tissue of the interatrial septum 134 heats up. The thermal sensor 131 measures the thermal response. A temperature-measuring circuit (not pictured) may be coupled to the thermal sensor.

This thermal sensing mechanism enables the physician to precisely locate the fossa ovalis 136. Specifically, the interatrial septum 134 exhibits a rate of temperature increase or decrease based on its naturally occurring cooling effects due to blood flow 138. In the case of the interatrial septum 134, blood flow 138 within the left atrium 140 will have a greater impact on the thermal response in areas where the tissue is thin. Because the fossa ovalis 136 is the thinnest portion of the septal wall, it encounters remarkably different cooling effects due to blood flow 138 compared to other portions of the interatrial septum. Thus, heating the interatrial septum 134 and monitoring the rates of temperature increase and decrease will permit the physician to locate the fossa ovalis 136.

Figure 8B:
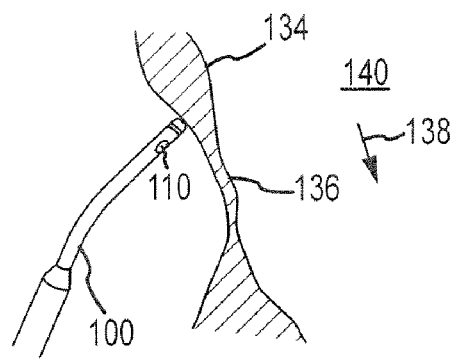
FIGS. 8B and 8C depict two different methods for locating a tissue structure using the tissue puncture assembly depicted in FIG. 8A.
Figure 8C:
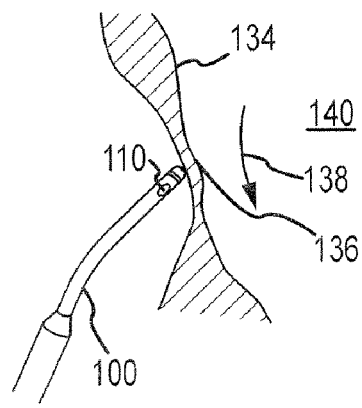

FIGS. 8B-8C depict two different methods for precisely locating the fossa ovalis 136 using the thermal sensing mechanism depicted in FIG. 8A. Generally speaking, these methods analyze the rate at which a tissue heats or cools. In FIG. 8B, RF energy is delivered between the first electrode 130 and the second electrode 132, and a portion of the interatrial septum 134 other than the fossa ovalis 136 is heated. Because the portion of the interatrial septum 134 other than the fossa ovalis 136 is thick compared to the fossa ovalis 136, it will exhibit a fast rise in temperature, and will likewise exhibit a slow decrease in temperature.

Conversely, when the fossa ovalis 136 is heated as shown in FIG. 8C, a slower rise in temperature will be seen. Additionally, the fossa ovalis 136 will exhibit a fast rate of cooling. Using these differential heating and cooling rates, the physician may precisely determine the location of the fossa ovalis 136 and avoid the adverse consequences associated with puncturing at an improper location.

Methods of puncturing a tissue will now be described. FIGS. 9A-E illustrate a schematic diagram exemplifying a tissue puncture procedure according to one embodiment of the present invention. In this procedure, the elongate tubular member 102 containing the flexible puncture member 118 is inserted into the right atrium 142. The distal tip 105 of the elongate tubular member 102 is urged against the interatrial septum 134 so that at least a portion of the interatrial septum 134 is adjacent to the side port opening 110 (see FIG. 9*a*). The distal end 120 of the flexible puncture member 118 is then advanced through the elongate tubular member 102, and deflects upon contacting guiding surface 108 to exit the side port 110 in a lateral direction relative to a longitudinal direction of the elongate tubular member 102.

Upon exiting the side port opening 110, the distal end 120 of the flexible puncture member 118 punctures the portion of the interatrial septum 134 adjacent the side port opening 110 (see FIG. 9*b*), and is advanced into the left atrium 140. In one aspect, the flexible puncture member 118 punctures the tissue at an oblique angle. In another aspect, the flexible puncture member 118 punctures the interatrial septum at the location of the fossa ovalis. The elongate tubular member 102 may include sensors, including thermal sensors, uni-polar or bi-polar electrodes, and ultrasound transducers and arrays, as described herein, to locate the fossa ovalis or to visualize the left atrial free wall.

After puncturing the interatrial septum, the distal end 120 of the flexible puncture member 118 automatically adopts a pre-formed, atraumatic shape to prevent puncturing structures or tissues within the left atrium, and becomes anchored within the left atrium 140 (see FIG. 9c). In some embodiments, the anchor shape may comprise one of a helical shape, a flower shape, or a basket shape. The elongate tubular member 102 is then advanced through the puncture site and into the left atrium 140 over the flexible puncture member 118 until the flexible puncture member 118 is fully contained within the elongate tubular member 102. As the elongate tubular member 102 is advanced over the distal end 120 of the flexible puncture member, the distal end returns to a straightened state (see FIGS. 9d-9e).

After puncturing the interatrial septum 134 according to the described method, a guidewire may be inserted through the lumen 144 (see FIGS. 3A-C) of the flexible puncture member 118 and into the left atrium 140. The elongate tubular member 102 and the flexible puncture member 118 may then be removed, and a medical device, such as an electrophysiology catheter may be advanced over the guidewire and into the left atrium 140. The electrophysiology catheter may comprise one of an ablation catheter, a diagnostic catheter, or a combination ablation and diagnostic catheter. Alternatively, prior to advancing the electrophysiology catheter over the guidewire, a dilator contained within a sheath may be advanced over the guidewire and into the left atrium 140. The guidewire and dilator are then removed and an electrophysiology catheter is advanced through the sheath and into the left atrium 140.

In another embodiment, a method of puncturing the pericardial sac is described. A flexible puncture member 118 contained within the lumen of an elongate tubular member 102 is inserted into a patient via a subxiphoid percutaneous approach. The distal portion 104 of the elongate tubular member 102 may optionally be equipped with one or more sensors to precisely locate the desired puncture location. In the subxiphoid percutaneous approach, the tissue puncture assembly 100 may be inserted at an angle between the left border of the subxiphoid process and the lower left rib. After insertion, the distal tip 105 of the elongate tubular member 102 is urged against the pericardial sac so that at least a portion of the pericardial sac is adjacent to the side port opening 110. The distal end 120 of the flexible puncture member 118 is then advanced through the elongate tubular member 102, and deflects upon contacting the guiding surface 108 to exit the side port 110 in a lateral direction relative to the longitudinal direction of the elongate tubular member 102.

Upon exiting the side port opening 110, the distal end 120 of the flexible puncture member 118 punctures the portion of the pericardial sac adjacent the side port opening 110, and is advanced into the pericardial space. In one aspect, the flexible puncture member 118 punctures the tissue at an oblique angle. Upon exiting the elongate tubular member 102, the distal end 120 of flexible puncture member 118 automatically adopts a pre-formed, atraumatic shape to prevent puncturing structures or tissues within the pericardial space, and becomes anchored within the pericardial space. The anchor shape may comprise one of a helical shape, a flower shape, or a basket shape. The elongate tubular member 102 is then advanced through the puncture site and into the pericardial space over the flexible puncture member 118 until the flexible puncture member 118 is fully contained within the elongate tubular member 102. As the elongate tubular member 102 is advanced over the distal end 120 of the flexible puncture member, the distal end returns to a straightened state (see FIGS. 9d-9e).

After puncturing the pericardial sac according to the described method, a guidewire may be inserted through a lumen 144 of the flexible puncture member 118 and into the pericardial space. The elongate tubular member 102 and the flexible puncture member 118 may then be removed, and a dilator contained within a sheath may be advanced over the guidewire and into the pericardial sac. The guidewire and dilator are then removed and an electrophysiology catheter is advanced through the sheath and into the pericardial sac. The electrophysiology catheter may comprise one of an ablation catheter, a diagnostic catheter, or a combination ablation and diagnostic catheter.

Although several embodiments of this invention have been described above with a certain degree of particularity, those skilled in the art could make numerous alterations to the disclosed embodiments without departing from the spirit or scope of this invention. For example, it is contemplated that persons of skill in the art could incorporate multiple sensors, electrodes and/or transducers into the tissue puncture assembly to visualize tissue structures and more precisely locate the desired puncture site. Further, although the invention has been described in connection with transseptal and pericardial access procedures, the devices and methods of the present invention can be used in connection with puncturing numerous tissue structures. For example, the devices and methods of the present invention can be utilized to puncture the interventricular septal wall to provide access to the left ventricle from the right ventricle. Additionally, although the distal end of the flexible puncture member is described as adopting a helical, basket, or flower shape, one of ordinary skill in the art will appreciate that other atraumatic, pre-formed shapes may also be utilized to good advantage in connection with the present invention.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:
1. A medical device comprising:
an elongate tubular member having a lumen extending therethrough in a longitudinal direction, wherein the elongate tubular member comprises
a distal portion having a wall;
a port opening extending through the wall, the port opening having a distal edge and a proximal edge; and a guiding surface within the lumen of the elongate tubular member, the guiding surface having a distal end, wherein the distal end of the guiding surface extends adjacent to the distal edge of the port opening; and a flexible puncture member insertable through the lumen of the elongate tubular member, the flexible puncture member having a distal portion and a proximal portion, wherein the flexible puncture member deflects upon contacting the guiding surface to exit the elongate tubular member through the port opening, and wherein the distal portion of the flexible puncture member is biased to assume a helix shape, a flower shape or a basket shape upon exiting the elongate tubular member, and wherein the flexible puncture member further comprises a lumen extending therethrough.

2. The medical device according to claim 1, wherein the distal portion of the flexible puncture member is straightenable for insertion within the elongate tubular member.

3. The medical device according to claim 1, wherein the flexible puncture member comprises a shape-memory alloy.

4. The medical device according to claim 3, wherein the shape-memory alloy comprises Nitinol.

5. The medical device according to claim 1, wherein a distal tip of the flexible puncture member is beveled.

6. The medical device according to claim 1 further comprising a guidewire insertable through the lumen of the flexible puncture member.

7. The medical device according to claim 1, wherein the distal portion of the elongate tubular member further comprises at least one electrode coupled to an impedance-measuring circuit.

8. The medical device according to claim 1, wherein the distal portion of the elongate tubular member further comprises at least one pair of electrodes coupled to an impedance-measuring circuit.

9. The medical device according to claim 1, wherein the distal portion of the elongate tubular member further comprises at least one thermal sensor coupled to a temperature-measuring circuit.

10. The medical device according to claim 1, wherein the port opening defines an outer perimeter, and wherein the outer perimeter of the port opening comprises at least one of an electrode or a thermal sensor.

11. The medical device according to claim 1, wherein the distal portion of the elongate tubular member further comprises at least one intravascular ultrasound sensor coupled to an image processor.

12. The medical device according to claim 1, wherein the distal portion of the elongate tubular member further comprises a plurality of ultrasound transducers in a phased array.

13. The medical device according to claim 12, wherein the plurality of ultrasound transducers are arranged in a linear phased array parallel to the longitudinal direction of the elongate tubular member.

14. The medical device according to claim 12, wherein the plurality of ultrasound transducers are arranged radially about the distal portion of the elongate tubular member in a circular phased array.

15. The medical device according to claim 1, wherein the distal portion of the elongate tubular member further comprises at least one ultrasound transducer, and wherein the at least one ultrasound transducer or a reflective surface which deflects the signal from the ultrasound transducer is rotatable relative to an axis of the elongate tubular member.

16. The medical device according to claim 1, wherein the port opening is positioned on the wall of the distal portion of the elongate tubular member such that the flexible puncture member exits therefrom in a lateral direction relative to the longitudinal direction of the elongate tubular member.

17. A medical device comprising:
an elongate tubular member having a lumen extending therethrough in a longitudinal direction, wherein the elongate tubular member comprises
a distal portion having a wall;
a port opening extending through the wall, the port opening having a distal edge and a proximal edge; and
a guiding surface within the lumen of the elongate tubular member, the guiding surface having a distal end, wherein the distal end of the guiding surface extends adjacent to the distal edge of the port opening; and
a flexible puncture member insertable through the lumen of the elongate tubular member, the flexible puncture member having a distal portion and a proximal portion,
wherein the flexible puncture member deflects upon contacting the guiding surface to exit the elongate tubular member through the port opening, and
wherein the distal portion of the flexible puncture member automatically adopts a first shape configured to puncture tissue upon exiting the elongate tubular member and a second pre-formed shape comprising at least one of a helix, a flower shape or a basket shape after the puncture member fully exits the port opening, and
wherein the flexible puncture member further comprises a lumen extending therethrough.

18. The medical device according to claim 17, wherein the second shape anchors the flexible puncture member in place.

* * * * *